United States Patent [19]

Alchas

[11] Patent Number: 4,737,152
[45] Date of Patent: Apr. 12, 1988

[54] CATHETER ASSEMBLY

[75] Inventor: Paul G. Alchas, Wayne, N.J.

[73] Assignee: Becton, Dickinson and Company, Franklin Lakes, N.J.

[21] Appl. No.: 881,148

[22] Filed: Jul. 2, 1986

[51] Int. Cl.⁴ .............................................. A61M 25/00
[52] U.S. Cl. ........................................ 604/256; 604/9; 604/247
[58] Field of Search ............... 604/105, 170, 247, 256, 604/8–10

[56] References Cited

U.S. PATENT DOCUMENTS

| | | | |
|---|---|---|---|
| 1,719,428 | 7/1929 | Friedman | 604/105 |
| 2,616,429 | 11/1952 | Merenlender | 604/105 |
| 3,111,125 | 11/1963 | Schulte | 128/350 |
| 3,799,172 | 3/1974 | Szpur | 604/105 |
| 4,549,879 | 10/1985 | Groshong et al. | 604/247 |
| 4,559,046 | 12/1985 | Groshong et al. | 604/105 X |

Primary Examiner—Dalton L. Truluck
Attorney, Agent, or Firm—John L. Voellmicke

[57] ABSTRACT

A catheter assembly, with active fluid control valve, includes a catheter having a cylindrical side wall describing a lumen therethrough, a proximal end and a closed distal end. The catheter includes a slit through the side wall positioned adjacent to the distal end. This slit is angularly oriented with respect to the longitudinal axis of the catheter and is defined by two opposed faces formed in the side wall. The catheter housing includes a conduit therethrough wherein the proximal end of the catheter is connected to the housing so that the conduit and the lumen are in fluid communication. The stylet is positioned within the lumen having a first end connected to the closed distal end and a second end. A valve control knob having a passageway therethrough is rotatably connected to the housing so that the passageway and the conduit are in fluid communication. Engagement structure is provided in the knob for engaging the stylet so that rotation of the knob relative to the housing causes rotation of the stylet which in turn causes rotation of the closed distal end of the catheter causing the opposed faces of the slit to separate forming an opening for allowing fluid communication between the lumen and the exterior of the catheter.

22 Claims, 3 Drawing Sheets

CATHETER ASSEMBLY

BACKGROUND OF THE INVENTION

1. Field of the Invention

The present invention relates to catheter assemblies and more particularly concerns a catheter having active fluid control valve features.

2. Description of Related Information

Various procedures such as a method of intravenous therapy known as hyperalimentation and certain regimens involving chemotherapeutic drugs require the use of a catheter which may remain in the patient's body for a period of days, weeks or even months. A typical procedure involves inserting the catheter through the subclavian vein, located near the collar bone, and advancing the catheter to the superior vena cava, an area of substantial blood flow of the heart. In some long term catheterization procedures the physician may reroute the exposed end of the catheter from the original entry, near the collar bone, subcutaneously through the patient's body and out in the abdominal area so that the patient can, in some cases, resume many normal activities without having a catheter protruding from his collar bone area.

These catheterization procedures are routinely performed with a conventional catheter having an open distal end. Blood flow out of the body is prevented by occluding a portion of the catheter which is external to the patient's body. In many instances, the portion of the catheter outside of the body is covered by an injection cap which includes a pierceable septum to allow injection and withdrawal of fluids through the septum. This type of catheter has disadvantages in that the open end of the catheter, which is positioned in the patient's body provides an area for the formation of blood clots. The potential for formation of clots is undesirable because clots can occlude the catheter and prevent therapy or a clot can separate from the catheter and travel to other areas of the vascular system and possibly cause injury by occluding a vessel. The type of catheter, having an open distal end, must be frequently flushed with a heparinized saline solution to clean the catheter area and reduce the potential for clot formation. This periodic maintenance, in itself, provides a potential for irritation by manipulation of the catheter and introduces an anticoagulant (heparin) into the blood stream which may affect the patient and/or blood test results. In addition, if the external cap is inadvertently removed, there is the danger of introducing an air embolus into a vein and potentially injuring the patient. Further, the blunt open end of the catheter interferes with blood flow and is believed to cause turbulent eddies in the area of the tip which may also promote clot formation.

Many of the above-recited problems could be eliminated if the central venous catheter were provided with a closed distal end portion. However, some type of port or valve means must then be provided. Schulte, in U.S. Pat. No. 3,111,125, teaches a ventriculo-atrial shunt apparatus comprising an inlet tube for placement in the cranial cavity, a manually operatable lamp subcutaneously implanted on the skull and an outlet tube extending between the pump and the atrium portion of the heart. Schulte's outlet tube has the desirable closed distal end and a plurality of slits around the periphery of the distal end of the tube acting as slit valves. Schulte teaches that fluid pressure in the tube will force the slits open so that fluid will flow freely when a sufficient pressure differential exists between the fluid within the tube and the area outside the tube.

Along these lines Groshong et al. (U.S. Pat. No. 4,559,046) teach a catheter device for intravenous therapy having a flexible closed distal end including a slit-type valve as described in Schulte and further including a twisted wire removable stiffener which can be used to facilitate insertion of the catheter into the patient and then removed. The distal end of the stiffener abuts against the interior closed end of the catheter when the stiffener is used to push the catheter through the vein. The stiffener does not occlude the catheter lumen.

It is desirable that a valve means in a central venous catheter should allow fluid flow through the catheter and into the patient, and fluid flow from the patient's vascular system out of the catheter which is desirable, for example, when obtaining a blood sample. Slit valves present a problem because inwardly directed pressure may tend, under some conditions, to shut the slit valve more tightly rather than to open it. Groshong et al., in U.S. Pat. No. 4,549,879, teach an improvement to make the slit valve more useful with respect to fluid flowing therethrough into the catheter. Groshong et al. teach that the use of stiff thermoplastic material in catheters has disadvantages in that the slit can cause damage to cellular elements which are injected into the body or withdrawn from the body through the slit. Groshong et al. teach the use of soft materials such as silicone rubber made in a thin cross-section and treated with dimethyl-siloxane for weakening and making the catheter wall more pliable in order to facilitate the two-way valve function.

The closed end catheters having slit-type valves overcome many of the deficiencies of the open end catheter as recited hereinabove. The closed end catheters having slit-type valves as taught by Schulte and Groshong et al. still have deficiencies. Most notably the slit-type valve is more adaptable to situations where outward flow is desirable and inward flow is not desirable because of its directional properties. Groshong et al. teach how to partially overcome this problem by making the catheter of soft material and weakening the structure around the valve so that it opens under a pressure differential in either direction. However, even the improved valves taught by Groshong et al. require a pressure differential for opening in either direction and therefore are not readily usable for certain tests involving pressure measurement using a transducer in the catheter assembly, such as measuring the central venous pressure, because the proximal open end of the catheter is not in free fluid communication with the vascular system. Also, it is still believed that the slit-type valve can cause damage to cellular elements passing through the valve because of the forces required to open the valve. Cells needed for blood testing may be damaged and cells being introduced into the vascular system may also be damaged. Further, as the distal end of the catheter is made of softer material and treated to be weaker and weaker in order to attempt to overcome the deficiencies of the pressure activated slit-valve, the tip of the catheter becomes weaker. This weakened tip is more prone to bending caused by patient movement or muscular movement within the patient's body, and the tip may be bent in such a manner as to open the valve in the absence of a fluid pressure differential across the valve. Accordingly, there is a tradeoff bevalve is responsive to fluid pressure differentials between the inside and the outside of the catheter, and providing a valve that stays shut during normal use conditions.

Catheters having closed distal ends and passive valve means have been addressed by the prior art, as alluded to above. However, there is still a need for a simple, straightforward, reliable, easily fabricated catheter having a closed distal end and active valve means which will minimize the potential for damage to cellular elements in liquid passing through the valve means and also minimize the potential for inadvertent opening of the valve which can result in patient blood loss or introduction of an air embolus into the patient's vascular system. It is also desirable to have a catheter assembly which will readily allow blood pressure determination using transducer devices connected to the catheter assembly.

SUMMARY OF THE INVENTION

The operable catheter assembly with active fluid control valve of the present invention comprises a catheter having a cylindrical side wall describing a lumen therethrough, a proximal end and a closed distal end. The catheter includes a slit through the side wall positioned adjacent to the distal end. The slit is angularly oriented with respect to the longitudinal axis of the catheter and is defined by two opposed faces formed in the side wall. Catheter housing means includes a conduit therethrough wherein the proximal end of the catheter is connected to the housing means so that the conduit and the lumen are in fluid communication. Stylet means within the lumen include a first end connected to the closed distal end of the catheter and a second end. A valve control knob includes a passageway therethrough and is rotatably connected to the housing means so that the passageway and the conduit are in fluid communication. Engagement means in the knob is provided for engaging the stylet means so that rotation of the knob relative to the housing means causes rotation of the stylet which in turn causes rotation of the closed distal end of the catheter causing the opposed faces of the slit to separate forming an opening for allowing fluid communication between the lumen and the exterior of the catheter.

The catheter assembly, with active fluid control valve, of the present invention includes a soft flexible catheter having a cylindrical side wall describing a lumen therethrough, a proximal end and a closed distal end. The catheter includes a slit through the side wall positioned adjacent to the distal end. This slit is angularly oriented with respect to the longitudinal axis of the catheter. The slit is defined by two opposed faces formed in the side wall. A catheter housing having a conduit therethrough is provided. The proximal end of the catheter is connected to this housing so that the conduit and the lumen are in fluid communication. Stiffening means for increasing the torsional rigidity of the catheter is positioned between the housing and the slit. A stylet wire within the lumen includes a first end connected to the closed distal end of the catheter and a second end. A valve control knob having a passageway therethrough is rotatably connected to the housing so that the passageway and the conduit are in fluid communication. Engagement means is provided in the knob for engaging the stylet so that rotation of the knob relative to the housing in a first rotational direction causes rotation of the stylet which in turn causes rotation of the closed distal end of the catheter causing the opposed faces of the slit to separate forming an opening for allowing fluid communication between the lumen and the exterior of the catheter, and rotation of the knob relative to the housing in a second rotational direction, opposite to the first rotational direction, causes rotation of the stylet which in turn causes rotation of the closed distal end of the catheter causing the opposed faces of the slit to close. The passageway, the conduit and the lumen form a continuous fluid path for allowing introduction of fluids into a patient or removal of fluids from a patient when the knob is rotated to open the slit. Stop means for limiting the rotational movement of the knob with respect to the housing to less than 360° is provided.

In accordance with the principles of the present invention, a number of advantages and objectives are attained. The present invention provides a simple, straight-forward, reliable, easily fabricated catheter having a closed distal end and an active valve means which will minimize the potential for damage to cellular elements in liquid passing through the valve means and also minimize the potential for inadvertent opening of the valve, during use, while allowing the operator to selectably open or shut the valve means regardless of pressure differentials between the catheter and the patient's venous system.

DETAILED DESCRIPTION

Figure 1:
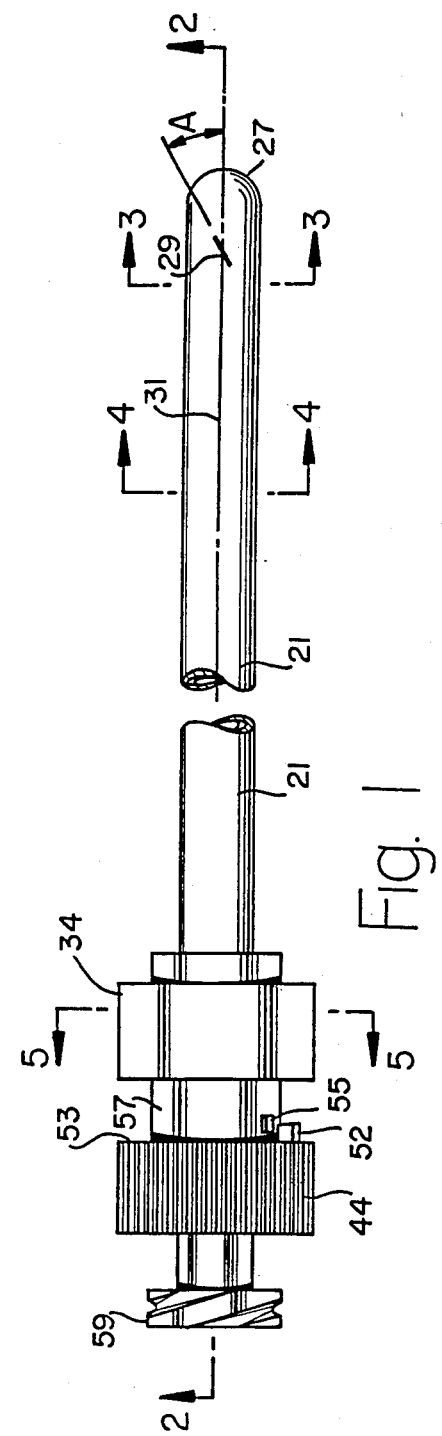
FIG. 1 is a side elevation view of the preferred catheter assembly of the present invention.
Figure 2:
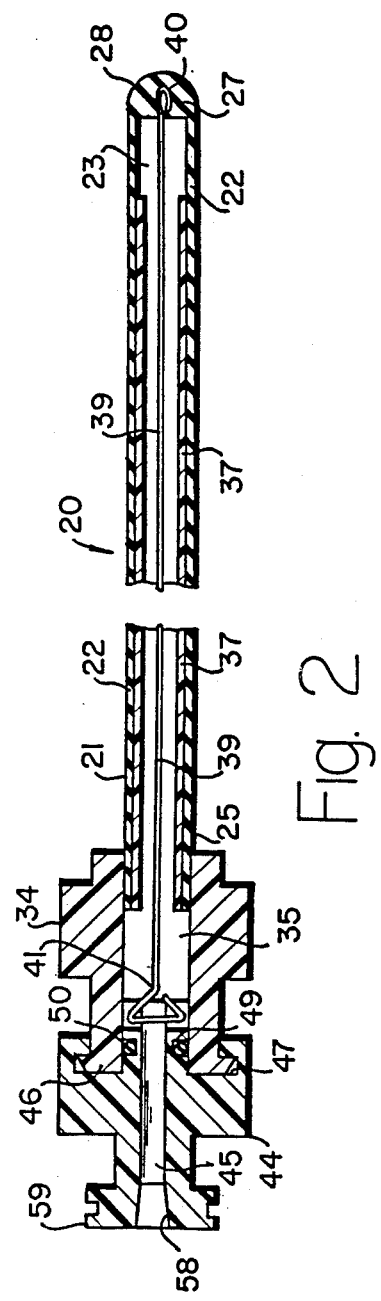
FIG. 2 is a partial cross-sectional view of the catheter assembly of FIG. 1 taken along line 2—2.
Figure 3:
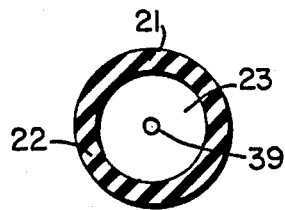
FIG. 3 is an enlarged cross-sectional view of the catheter assembly of FIG. 1 taken along line 3—3.
Figure 4:
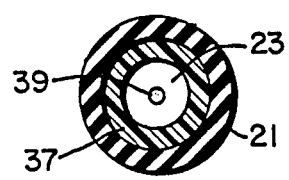
FIG. 4 is an enlarged cross-sectional view of the catheter assembly of FIG. 1 taken along line 4—4.
Figure 5:
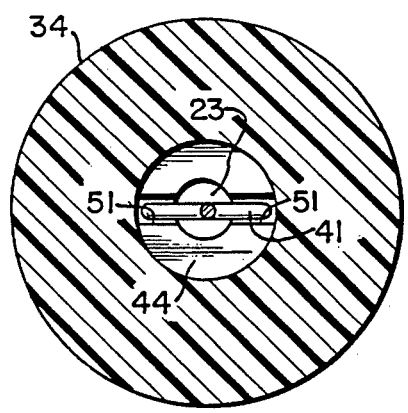
FIG. 5 is an enlarged cross-sectional view of the catheter assembly of FIG. 1 taken along line 5—5.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 6, a catheter assembly 20 with active control valve features includes a flexible catheter 21 having a cylindrical side wall 22 describing a lumen 23 therethrough, a proximal end 25 and a closed distal end 27 which, in this preferred embodiment, has a rounded exterior surface 28 to facilitate insertion of the catheter into the patient. For purposes of the description of the present invention, the term "distal" is meant to refer to that end of the element which is furthest from the person holding the catheter, whereas the term "proximal" is meant to refer to the end of the element closest to the holder of the catheter.

Catheter 21 includes a slit 29 through side wall 22 adjacent to distal end 27. The slit is angularly oriented with respect to longitudinal axis 31 of the catheter, illustrated as angle "A" in FIG. 1. The slit is defined by two opposed faces 32 and 33 formed in the side wall. As will be explained in more detail hereinafter, it is desirable to have the slit slanted at an angle within the range of about 10° to 80° with respect to the longitudinal axis of the catheter and it is preferred that the angle be within the range of about 20° to 40° with respect to the longitudinal axis.

The proximal end of the catheter is connected to a catheter housing 34 having a conduit 35 therethrough. Conduit 35 in the catheter housing and lumen 23 in the catheter are in fluid communication.

A stiffening means for increasing the torsional rigidity of the catheter is provided in the form of a cylindrically-shaped stiffening member 37. In this preferred embodiment the stiffening member has an outside diameter which is larger than the inside diameter of the catheter, before assembly. Upon assembly, the catheter is stretched over the stiffening member providing an intimate contact between the outside surface of the stiffening member and the inside surface of the catheter lumen along the length of the stiffening member which preferably runs from about the catheter housing toward the proximal end of the catheter to a position which is located proximally to the slit in the catheter.

It is also practical and desirable to produce a catheter assembly wherein the outside diameter of the stiffening member is equal to or slightly less than the inside diameter of the catheter. As will become apparent hereinafter, rotation of the closed distal end of the flexible catheter will cause the sidewall of the catheter to contact the outside of the stiffening member. After contact is made, the stiffening member will increase the torsional rigidity of the catheter assembly. Also, the assembly of the various catheter components, wherein the stiffening member is of equal or smaller outside diameter than the inside diameter of the flexible catheter will be made easier because less force will be required to position the stiffening member within the catheter.

In this preferred embodiment the catheter is held firmly with respect to the housing by virtue of a slight interference fit wherein the catheter, with stiffening member, has an outside diameter slightly larger than the inside diameter of conduit 35 in housing 34. Accordingly, the catheter and stiffener are forced into conduit 35 creating an interference fit. Also, adhesive is used at the interface of the catheter and the conduit to further strengthen this connection. It will be apparent to one skilled in the art that numerous methods may be used to join a catheter and a housing. Such methods include the use of adhesives, ultrasonic welding, internally positioned metal grommets or tubes which are large enough to provide considerable anchoring force between the catheter and the housing, and the like. The structure used to bind the catheter to the housing, as described hereinabove, is exemplary of these many possibilities.

Stylet means preferably in the form of a stylet wire 39 is positioned within the lumen of the catheter, having a first end 40 connected to closed distal end 27 of the catheter and a second end 41 which in this preferred embodiment is formed into a loop-shaped structure 43 so that the loop is integrally formed of stylet wire. The stylet wire outside diameter is smaller than the catheter inside diameter and the stiffening member inside diameter, so that the stylet wire does not prevent fluid flow through the lumen of the catheter or through the inside of the stiffening member.

A valve control knob 44, having a passageway 45 therethrough, is rotatably connected to catheter housing 34 so that passageway 45 is in fluid communication with conduit 35. Valve control knob 34 and catheter housing 34 are held together by virtue of proximal flange 46 on the catheter housing which engages rotational groove 47 in the valve control knob. This structure allows the valve control knob to rotate with respect to the catheter housing but keeps the two elements from coming apart. It is preferred that the catheter housing and the valve control knob be designed so that the proximal flange can be snap-fitted into the passageway to avoid use of additional components. Further, to provide a fluid-tight seal and to prevent fluid passing through passageway 45 and conduit 35 from leaking out between the housing and the control knob, O-ring groove 49 is provided in the control knob and contains O-ring 50. The O-ring presses against the side wall of conduit 35 to help prevent leakage of fluid. It will be apparent to one skilled in the art that there are numerous structures for joining components having conduits in fluid communication wherein the components must be rotatable with respect to each other. In high pressure applications these designs may become very complex involving gasket and packing material and means to contain this material. In a simple low pressure application it may be possible to choose materials and tolerances so that the fluid containment requirement is meant without any additional parts such as O-rings and the like. Accordingly, the structure described hereinabove to provide a fluid-tight seal between the housing and the valve control knob while still allowing the relative rotation of these components is exemplary of these many possibilities.

Engagement means is provided in knob 44 for engaging the stylet wire so that rotation of the knob relative to catheter housing 35 causes rotation of the stylet. In this preferred embodiment the engagement means comprises a slot 51 in valve control knob 44, on both sides of passageway 45. Slot engaging means preferably in the form of the loop-shaped structure on the second end of the stylet wire engages the slot on both sides of the passageway so that rotation of the knob will cause rotation of the stylet. Again, it will be apparent to one skilled in the art that there are numerous constructions which can be used to engage a stylet and a knob so that rotation of the knob causes rotation of the stylet including bonding or joining the stylet to the knob or various containment structures and that the structure described hereinabove is exemplary of those many possibilities.

Proximal end 58 of passageway 45 in the valve control knob is preferably frusto-conically shaped for accepting the tapered tip of fluid transfer devices such as hypodermic syringe assemblies, and various tubing sets and valves which incorporate frusto-conically shaped tapered tips having fluid passageways therein. Also provided is external thread portion 59 on the proximal end of valve control knob 44 for engaging known fluid transfer devices having locking luer type fittings, such as hypodermic syringe assemblies.

Figure 6:
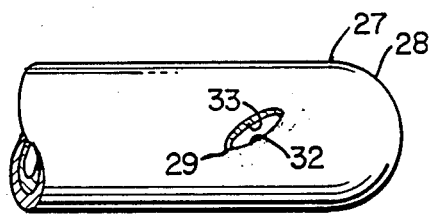
FIG. 6 is a partial side elevation view of the catheter including the distal end of the catheter, illustrating the slit valve in an open position.

Rotation of valve control knob 44 with respect to catheter housing 34 can be achieved by holding the catheter housing with one hand and rotating the valve control knob with the other. Rotation of valve control knob 44 with respect to housing 34 in a first rotational direction, which in the case of the preferred embodiment is the clockwise direction when viewed from the proximal end of the catheter assembly along the longitudinal axis of the catheter, causes rotation of the stylet in that direction and in turn causes rotation of the closed distal end of the catheter causing the opposed faces of slit 29 to separate, as best illustrated in FIG. 6. The opening of the slit or the separation of the side walls is caused by the twisting of the catheter in the area of the slit. In a long catheter, the stiffening means prevents or minimizes twisting along most of the length of the catheter so that the rotation of the distal end of the catheter causes twisting of the catheter along the length of the catheter between the distal end of the catheter and the distal end of the stiffening means which is the area of the slot. It is within the purview of the instant invention to include a catheter without a stiffening means. However, where the catheter length is long the stiffening means allows opening the valve with the minimum angular displacement of the control knob.

In use, the catheter of the instant invention is placed in the patient, as for example where the catheter enters the subclavian vein and is positioned so that the distal end of the catheter is in the area of the superior vena cava. At this point, a therapeutic liquid may be introduced into the patient's vascular system. This fluid introduction is accomplished by rotating the valve control knob in the direction to open the slit and fluid, for example, from a syringe, may be forced through passageway 45, conduit 35 and lumen 23 of the catheter through the open slit and into the patient's vascular system. Unlike prior art catheters having slit valves, the valve in the instant invention is held open so that additional pressure is not required to open the valve. In cases where blood is being provided to the patient the potential for damaging cells which must be forced through the normally closed slit valves of the prior art invention is minimized because the instant invention provides a clear fluid path from the lumen to the patient's vascular system. The capacity of the instant invention to hold the slit valve in an open position, regardless of pressure differential between the interior and the exterior of the catheter is a major advantage of the instant invention over the catheters having slit valves of the prior art.

When it is no longer desired to have the slit of the catheter open the user may turn the valve control knob in a second rotational direction, opposite of the first rotational direction, with respect to the catheter housing. This rotation causes rotation of the stylet which in turn causes rotation of the closed distal end of the catheter causing the opposed faces of the slit to close.

In the preferred embodiment a stop means is provided for limiting the rotational movement of the knob with respect to the catheter housing to less than 360°. There are numerous structures which can be used to prevent joined parts from rotating with respect to each other for more than 360°. These structures usually involve projections on both parts which will contact at a certain position in rotation and prevent further rotation. In the preferred embodiment projection 52 extends axially from surface 53 to the valve control knob and is capable of contacting protuberance 55 which projects radially outwardly from surface 57 of the catheter housing so that the valve control knob is prevented from rotating more than 360° with respect to the catheter housing. It is also preferred that the catheter assembly of the present invention be provided with position indicia (not shown) on the housing and an indicator means on the knob (not shown) so that the user can determined whether said slit is open or closed by observing the relative position of said indicator means with respect to said position indicia.

It should be noted that because the present invention provides structure for holding the slit closed or holding the slit open that the structure at the distal end of the catheter, including choice of materials, can be designed for optimum performance because the additional requirement of valve opening or closing at predetermined pressure differentials is substantially eliminated. The prior art catheters require a substantial design effort to achieve opening pressures that are workable, including limitations on materials and specific processes to weaken the structure of the valve. Even if performance characteristics are arguably achieved the possible disadvantage of possible damage to cellular components being passed through the valve is still present and blood pressure measurements involving, for example, placing a transducer at the proximal end of the catheter, cannot be performed with accuracy because of the pressure needed to open the valve. The present invention, however, allows the valve to be opened for a transducer facilitated blood pressure test.

Along these lines, with the ability to actively select an open or shut position for the slit valve it is now possible to design the valve shape for maximum performance, for example, smooth surfaces for fluid flow or to optimize the area of the opening. Accordingly, various slit configurations such as a curvilinear shape may be used to optimize performance. Even a slit which is not normally shut when the catheter is at rest position may be used because of the instant invention's ability to open and shut the slit. It is preferred that the valve control knob and the catheter housing be designed so that when the valve control knob is rotated to open or close the valve that the frictional forces between the knob and the housing will be strong enough to keep the valve in the open or closed position.

Figure 7:
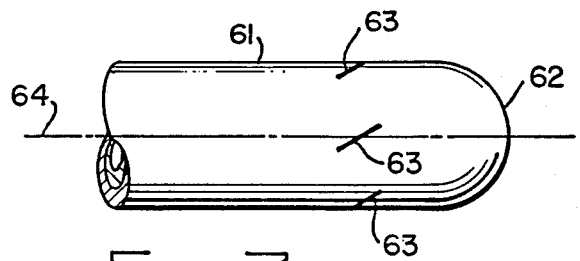
FIG. 7 is a partial side elevation view of another embodiment of the catheter of the present invention illustrating a portion of the catheter including a distal tip and a plurality of slit valves.

Referring to FIG. 7, another embodiment of the present catheter assembly with active fluid control valve is substantially similar to the embodiment of FIGS. 1-6, with the exception of the structure of the distal end of the catheter, illustrated in FIG. 7. Flexible catheter 61 of this embodiment includes a cylindrical side wall describing a lumen (not shown) therethrough and a distal closed end 62. Catheter 61 includes a plurality of slits 63. Each slit is angularly oriented with respect to longitudinal axis 64 of the catheter. Each slit is defined by two opposed faces formed in the side wall. In this embodiment the slit is substantially straight and the opposed faces are substantially planar. The catheter assembly of this embodiment functions substantially similarly to the embodiment of FIGS. 1-6. However, the additional slits may provide substantially increased flow area between the lumen and the exterior of the catheter or comparable flow area with less control knob rotation with respect to the catheter housing.

A wide variety of rigid materials are suitable for the catheter housing and the valve control knob with thermoplastic materials such as polyurethane, polypropylene, polyethylene and polystyrene being preferred. A wide variety of flexible materials such as natural rubber, synthetic rubber and thermoplastic elastomers are suitable for forming the catheter, with silicone rubber being desirable and polyurethane being preferred. The stylet may be made of a wide range of materials with stainless steel wire being preferred. The stylet may be anchored to the distal end of the catheter via the use of adhesives, or by forming the tip with the stylet properly positioned, and the like. The method of connecting the stylet to the distal end of the catheter may be determined by the material selected from the catheter.

Thus, it can be seen that the present invention provides a simple, straightforward, reliable, easily fabricated catheter having a closed distal end and an active valve means which will minimize the potential for damage to cellular elements in liquid passing through the valve means and also minimize the potential for inadvertent opening while allowing the operator to selectably open or shut the valve means regardless of pressure differentials between the catheter and the patient's venous system.

What is claimed is:

1. A catheter assembly with active fluid control valve for vascular therapy comprising:
   a flexible catheter adapted for insertion into the vascular system having a cylindrical side wall describing a lumen therethrough, a proximal end and a closed distal end;
   said catheter including a slit through said side wall positioned adjacent to said distal end, said slit being angularly oriented with respect to the longitudinal axis of said catheter, said slit being defined by two opposed faces formed in said side wall;
   a catheter housing having a conduit therethrough, said proximal end of said catheter being connected to said housing so that said conduit and said lumen are in fluid communication;
   stiffening means for increasing the torsional rigidity of said catheter positioned between said housing and said slit;
   a stylet wire within said lumen having a first end connected to said closed distal end of said catheter;
   a valve control knob having a passageway therethrough rotatably connected to said housing so that said passageway and said conduit are in fluid communication; and
   engagement means in said knob for engaging said stylet so that rotation of said knob relative to said housing in a first rotational direction causes rotation of said stylet which in turn causes rotation of said closed distal end of said catheter causing said opposed faces of said slit to separate forming an opening for allowing fluid communicating between said lumen and the exterior of said catheter and rotation of said knob relative to said housing in a second rotational direction, opposite to said first rotational direction, causes rotation of said stylet, which in turn causes rotation of said closed distal end of said catheter causing said opposed faces of said slit to close, said opposed faces of said slit being capable of separation without causing substantial radial expansion of said cylindrical side wall in the area of said slit.

2. The catheter assembly of claim 1 wherein said stiffening means includes a cylindrically shaped stiffening member positioned within said lumen extending from said catheter housing toward said slit.

3. The catheter assembly of claim 2 wherein said stiffening member has a larger outside diameter than the inside diameter of said catheter so that when assembled said catheter is stretched over said stiffening member.

4. The catheter assembly of claim 1 wherein said stiffening means includes a portion of said catheter having a smaller inside diameter making said side wall thicker along the catheter between said catheter housing and said slit.

5. The catheter assembly of claim 1 wherein there is a plurality of slits all being positioned adjacent to said distal end.

6. The catheter assembly of claim 1 where said slit is substantially straight and said opposed faces being substantially planar.

7. The catheter assembly of claim 1 wherein said slit is oriented at an angle within the range of about 10° to 80° with respect to the longitudinal axis of said catheter.

8. The catheter assembly of claim 1 wherein said slit is oriented at an angle within the range of about 20° to 40° with respect to the longitudinal axis of said catheter.

9. The catheter assembly of claim 1 wherein said slit is curvilinearly shaped.

10. The catheter assembly of claim 1 wherein said engagement means includes a slot in said knob on both sides of said passageway and slot engaging means at said second end of said stylet, said slot engaging means being positioned within said slot on both sides of said passageway so that rotation of said knob with respect to said housing will cause said stylet to rotate.

11. The catheter assembly of claim 10 wherein said slot engaging means includes a loop-shaped structure formed in said second end of said stylet wire comprising a portion of said stylet wire.

12. The catheter assembly of claim 1 wherein said passageway at the proximal end of said knob is frustoconically shaped for accepting the tapered tip of a fluid transfer device.

13. The catheter assembly of claim 1 further including stop means for limiting the rotational movement of said knob with respect to said housing to less than 360°.

14. The catheter assembly of claim 13 further including position indicia on said housing and indicator means on said knob positioned so that the user can determine whether said slit is open or closed, by observing the relative position of said indicator means with respect to said position indicia.

15. The catheter assembly of claim 1 further including biasing means for biasing said knob in a rotational direction with respect to said housing so that said slit will be normally closed, said biasing means being capable of returning said slit to a closed position when said knob is free of externally applied forces.

16. The catheter assembly of claim 2 wherein said stiffening member is made of thermoplastic material.

17. The catheter assembly of claim 1 wherein said catheter is made from materials selected from the group consisting of natural rubber, synthetic rubber and thermoplastic elastomers.

18. The catheter assembly of claim 17 wherein the thermoplastic elastomer is polyurethane.

19. An operable catheter assembly with active fluid control valve for vascular therapy comprising;
   a flexible catheter adapted for insertion into the vascular system having a cylindrical side wall describing a lumen therethrough, a proximal end and a closed distal end;
   said catheter including a slit through said side wall positioned adjacent to said distal end, said slit being angularly oriented with respect to the longitudinal axis of said catheter, said slit being defined by two opposed faces formed in said side wall;
   a catheter housing means having a conduit therethrough, said proximal end of said catheter being connected to said housing means so that said conduit and said lumen are in fluid communication;

stiffening means for increasing the torsional rigidity of said catheter positioned between said housing and said slit;

stylet means within said lumen having a first end connected to said closed distal end of said catheter, and a second end;

a valve control knob having a passageway therethrough rotatably connected to said housing means so that said passageway and said conduit are in fluid communication; and engagement means in said knob for engaging said stylet means so that rotation of said knob relative to said housing means causes rotation of said stylet which in turn causes rotation of said closed distal end of said catheter causing said opposed faces of said slit to separate forming an opening for allowing fluid communicating between said lumen and the exterior of said catheter, said opposed faces of said slit being capable of separation without causing substantial radial expansion of said cylindrical side wall in the area of said slit.

20. A catheter assembly with active fluid control valve for vascular therapy:

a soft flexible catheter adapted for insertion into the vascular system having a cylindrical side wall describing a lumen therethrough, a proximal end and a closed distal end;

said catheter including a slit through said side wall positioned adjacent to said distal end, said slit being angularly orinted with respect to the longitudinal axis of said catheter, said slit being defined by two opposed faces formed in said side wall;

a catheter housing having a conduit therethrough, said proximal end of said catheter being connected to said housing so that said conduit and said lumen are in fluid communication;

stiffening means for increasing the torsional rigidity of said catheter positioned between said housing and said slit;

a stylet wire within said lumen having a first end connected to said closed distal end of said catheter, and a second end;

a valve control knob having a passageway therethrough rotatably connected to said housing so that said passageway and said conduit are in fluid communication;

engagement means in said knob for engaging said stylet so that rotation of said knob relative to said housing in a first rotational direction causes rotation of said stylet which in turn causes rotation of said closed distal end of said catheter causing said opposed faces of said slit to separate forming an opening for allowing fluid communication between said lumen and the exterior of said catheter and rotation of said knob relative to said housing in said second rotational direction, opposite to said first rotational direction, causes rotation of said stylet which in turn causes rotation of said closed distal end of said catheter causing said opposed faces of said slit to close;

said passageway, said conduit and said lumen forming a continuous fluid path for allowing introduction of fluids into a patient or removal of fluids from a patient when said knob is rotated to open said slit; and stop means for limiting the rotational movement of said knob with respect to said housing to less than 360°, said opposed faces of said slit being capable of separation without causing substantial radial expansion of said cylindrical side wall in the area of said slit.

21. The catheter assembly of claim 20 wherein said stiffening means includes a cylindrically shaped stiffening member positioned within said lumen extending from said catheter housing toward said slit.

22. The catheter assembly of claim 20 wherein said slit is substantially straight and said opposed faces being substantially planar.

* * * * *